United States Patent [19]

Hamano et al.

[11] Patent Number: 4,678,640
[45] Date of Patent: Jul. 7, 1987

[54] INDICATOR FOR DETECTING RESIDUAL ETHYLENE OXIDE

[75] Inventors: Masanori Hamano, Koshigaya; Siro Takeuchi, Gyoda; Ichiro Inoue, Hino, all of Japan

[73] Assignee: Ekika Carbon Dioxide Co., Ltd., Tokyo, Japan

[21] Appl. No.: 799,198

[22] Filed: Nov. 18, 1985

Related U.S. Application Data

[63] Continuation of Ser. No. 355,368, Mar. 8, 1982, abandoned.

[30] Foreign Application Priority Data

Mar. 17, 1981 [JP] Japan .................................. 56-37318

[51] Int. Cl.⁴ .......................................... G01N 31/22
[52] U.S. Cl. ........................................ 422/56; 422/57; 422/58; 422/87; 436/1; 436/93
[58] Field of Search ............... 422/55, 56, 57, 58, 422/83, 86, 87; 436/1, 93

[56] References Cited

U.S. PATENT DOCUMENTS

| | | | |
|---|---|---|---|
| 2,998,306 | 8/1961 | Huyck et al. | 422/56 |
| 3,627,469 | 12/1971 | Cheng | 23/232 R |
| 3,738,811 | 6/1973 | Cheng | 436/1 |
| 3,992,154 | 11/1976 | Whitbowine et al. | 422/34 |
| 4,094,642 | 6/1978 | Sumimoto et al. | 422/57 |
| 4,138,216 | 2/1979 | Larson et al. | 422/56 |
| 4,195,058 | 3/1980 | Patel | 422/56 |
| 4,436,819 | 3/1984 | Manning | 436/1 |
| 4,495,291 | 1/1985 | Lawton | 436/1 |

FOREIGN PATENT DOCUMENTS

| | | |
|---|---|---|
| 53-138393 | 1/1978 | Japan . |
| 53-21871 | 6/1978 | Japan . |
| 854142 | 11/1960 | United Kingdom . |
| 1506401 | 4/1978 | United Kingdom . |
| 1523277 | 8/1978 | United Kingdom . |

OTHER PUBLICATIONS

Brewer, et al., "Biological-Chemical Indicator For Ethylene Oxide Sterilization"-Journal of Pharmaceutical Science, vol. 55, No. 1, pp. 57-59 (1961).

Primary Examiner—David L. Lacey

[57] ABSTRACT

An indicator for detecting residual ethylene oxide comprising a substrate impregnated with a solution of 4-(4-nitrobenzyl)pyridine and an envelope of the substrate which is at least partially transparent and has low permeability to gaseous ethylene oxide is provided, the envelope being preferably made of a transparent plastic film. With the indicator, an amount of ethylene oxide remaining in various medical instruments, etc. may be estimated by the naked eye since the color of the indicator changes step by step in the course of the release of residual ethylene oxide.

10 Claims, 6 Drawing Figures

INDICATOR FOR DETECTING RESIDUAL ETHYLENE OXIDE

This application is a continuation, of application Ser. No. 355,368, filed Mar. 8, 1982, now abandoned.

This invention relates to an indicator which enables to estimate with the naked eye an amount of gaseous ethylene oxide (hereinafter referred to as "EOG") remaining in medical instruments or sanitary goods sterilized with EOG by the colour or the color-change of the indicator.

Sterilization of medical instruments or sanitary goods is carried out by EOG alone, a mixture of EOG and chlorofluorohydrocarbon or a mixture of EOG and carbon dioxide ($CO_2$). On the other hand, since toxicity of EOG is fairly high, sterilization with EOG is frequently accompanied by various harmful influences, for instance, chemical burns, injuries of the skin and mucous membranes and hemolysis, which have attracted the world-wide attention.

Regarding the injuries on living bodies by the residual EOG in the objects sterilized with EOG as importance, Food and Drug Administration (FDA) of the United States regulates the acceptable concentration of residual EOG to less than 25 ppm in the articles to be embedded in living bodies and to less than 250 ppm in the articles to be contacted with the outer side of living bodies.

As a method for quantitative analysis of the residual EOG, gas chromatography and colorimetric analysis are used at present, and both methods require expensive apparatus for analysis and skilled technicians for manipulating the apparatus. In addition, it takes a considerably much time to obtain the analytical results. Consequently, at present the amount of residual EOG in the sterilized objects is only estimated while referring to the data obtained by organizations specified in analysis or published in scientific or medical literatures. However, between these cases and practical cases, there exist many differences regarding the conditions of sterilizations, the materials of the objects to be sterilized and the packing conditions of the objects. As the result, the courses of release of EOG are different. Accordingly, it is quite inaccurate to judge the amount of residual EOG based on these data.

Under these situations, in the manufacturers of medical instruments and the material supplying centers in hospitals, there are strong demands for the method and apparatus for estimating instantly and easily the amount of residual EOG in the sterilized objects, however such demands have not hitherto been fulfilled.

It is an object of the invention to provide an indicator by which the amount of residual EOG can be estimated with the naked eye.

The indicator of the invention comprises a substrate impregnated with a solution of 4-(4-nitrobenzyl)pyridine (hereinafter referred to as NBP), namely, a color-changing site, and an envelope which encloses the substrate therein and has a low permeability to EOG.

The invention will be explained in detail while referring to the drawings.

The substrate 1 of the indicator of the invention is a sheet of paper impregnated with a solution of NBP at a concentration of 0.5 to 5% by weight, preferably 2 to 3% by weight in an organic solvent such as ethanol, isopropyl alcohol, ethyl acetate, acetone, methyl ethyl ketone and the like, and thereafter dried, the paper being selected from materials easily impregnated with the solution, preferably being synthetic paper, blotting paper or filter paper.

The envelope 2 which encloses the substrate 1 is at least partially transparent so that the colour-change of the substrate 1 can be observed by the naked eye, and the permeability of the envelope to EOG should be substantially low, preferably not more than 200 ml/100.inch$^2$/mil/24 hr at 25° C. under the atmospheric pressure and 50% R.H. to $CO_2$ measured according to ASTM D 1434-63.

It is unnecessary to have the envelope 2 closely adhered to the substrate 1, and it is required that the envelope 2 encloses perfectly the substrate 1 to prevent the invasion of air from outside, for instance, as a sealed pouch.

Figure 1:
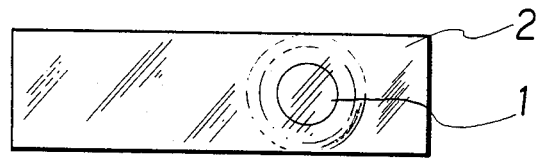
FIG. 1 is a plane view of an indicator of the invention.
Figure 2:
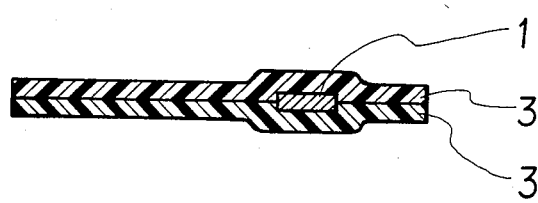
FIG. 2 is a cross sectional view of a flake-like indicator of the invention.

Transparent and heat-sealable plastic films may be used as the material for the envelope 2. Such a film may be a single-layer film 3 (as in FIG. 2) and may be a composite film 4, 5 (as in FIG. 3). As the single-layer film 3, a polyvinyl alcohol film or a nylon film is preferably utilized with a preferable thickness of 5 to 40 microns. The composite film for use as the envelope 2 comprises an outer layer 4 having low permeability to EOG and an inner layer having high permeability to EOG and heat-sealability. As the material for the outer layer 4, polyester, nylon, polyvinyl alcohol, polyvinylidene chloride, polyvinyl fluoride or cellophane is preferable with the preferable thickness of 5 to 40 microns. As the material for the inner layer 5, polyethylene or polypropylene is preferable, and the thickness of the inner layer may be even a little thicker than that of the outer layer.

Figure 4:
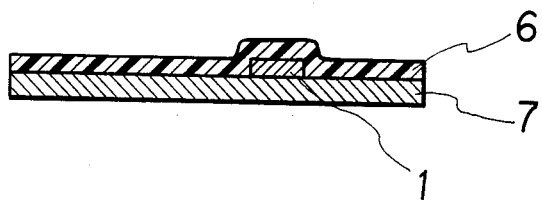
FIG. 4 is a cross sectional view of a still another indicator of the invention.

In addition, as another envelope fulfilling the above-mentioned conditions, a composite material as shown in FIG. 4 may be used, which is manufactured by adhering a plastic film 6 having low permeability to EOG onto a base plate 7 such as a metal foil, for example aluminum foil, which is impermeable to EOG while putting the substrate 1 between the plastic film 6 and the base plate 7. Namely, the plastic film 6 contacts to one side of the substrate 1, and the base plate 7 contacts to the other side of the substrate 1. Naturally, in this case, as the plastic film 6, either the above-mentioned single film or the composite film may be utilized.

Figure 5:
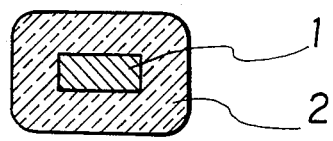
FIG. 5 is a cross sectional view of a tablet-like indicator of the invention.

The form of the indicator for detecting residual EOG of the invention may be a flake-like as shown in FIGS. 1 to 4, or a tablet-like as shown in FIG. 5. The envelope of the tablet-like indicator may be a single- or a composite film.

The color of the indicator of the invention changes step-wise as follows;

light blue→blue→dark blue→grey→brown→light brown→yellow in the course of release of EOG, and the time required for changing into each color is the same if the conditions of sterilization and release of EOG are the same. Accordingly, when the relationship between the amount of residual EOG measured by gas chromatography or the like and the time required for the indicator of the invention to change into each color is established in each material of medical instruments sterilized under the general sterilization conditions, the amount of residual EOG may be visually estimated by placing the indicator of the invention together with the object to be sterilized. Namely, by the indicator of the invention, it may be indirectly judged whether the concentration of residual EOG in the object has come to be lower than the predetermined value or the regulated value by FDA. It is known that the release rate of EOG from a sterilized object is very different according to the conditions of sterilization, the materials and its states of the object including the package thereof to be sterilized and the conditions under which the sterilized object is left. However, if the conditions of sterilization and the materials of objects to be sterilized have been predetermined, the amount of residual EOG in the objects after sterilization can be estimated by observing the color change of the indicator of the invention as is shown in the following Examples.

The invention will be further illustrated more in detail while referring to the following non-limiting Examples. It will be evident to those skilled in the art that variations can be made without departing from the spirit and the scope of the invention as defined in the claims which follow this specification.

EXAMPLE 1

Figure 3:
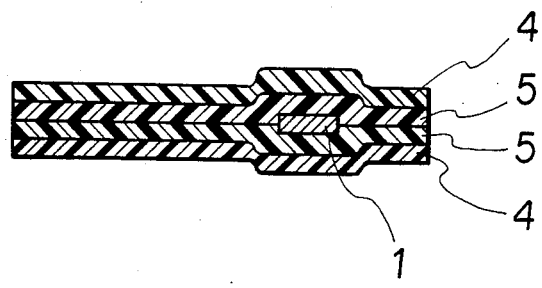
FIG. 3 is a cross sectional view of an another flake-like indicator of the invention.

Onto a sheet of filter paper of 10 mm in diameter and 0.5 mm in thickness, 0.05 ml of a 2% by weight acetone solution of NBP was dropped, and after drying the sheet in open air, the dried sheet was packaged by heat-sealing in a composite film (60×20 mm) comprising a polyester film (permeability to $CO_2$ of 50 ml/100 inch$^2$/mil/24hr) of 12 microns in thickness as the outer layer and a cast polypropylene film of 40 microns in thickness as the inner layer to prepare an indicator of the invention shown in FIG. 3.

After introducing the prepared indicator alone into a sterilizer, the indicator was treated with a gaseous mixture consisting of 30% by volume of EOG and 70% by volume of $CO_2$ at 50° C. and the concentration of EOG of 500 mg/liter for 2 hours, and then removed from the sterilizer to be left stand in a room at 25° C.

At the time when the sterilization of the indicator was over, it was colourless, however, as the time passed by, it showed the following colour change as is shown in Table 1:

TABLE 1

Figure 6:
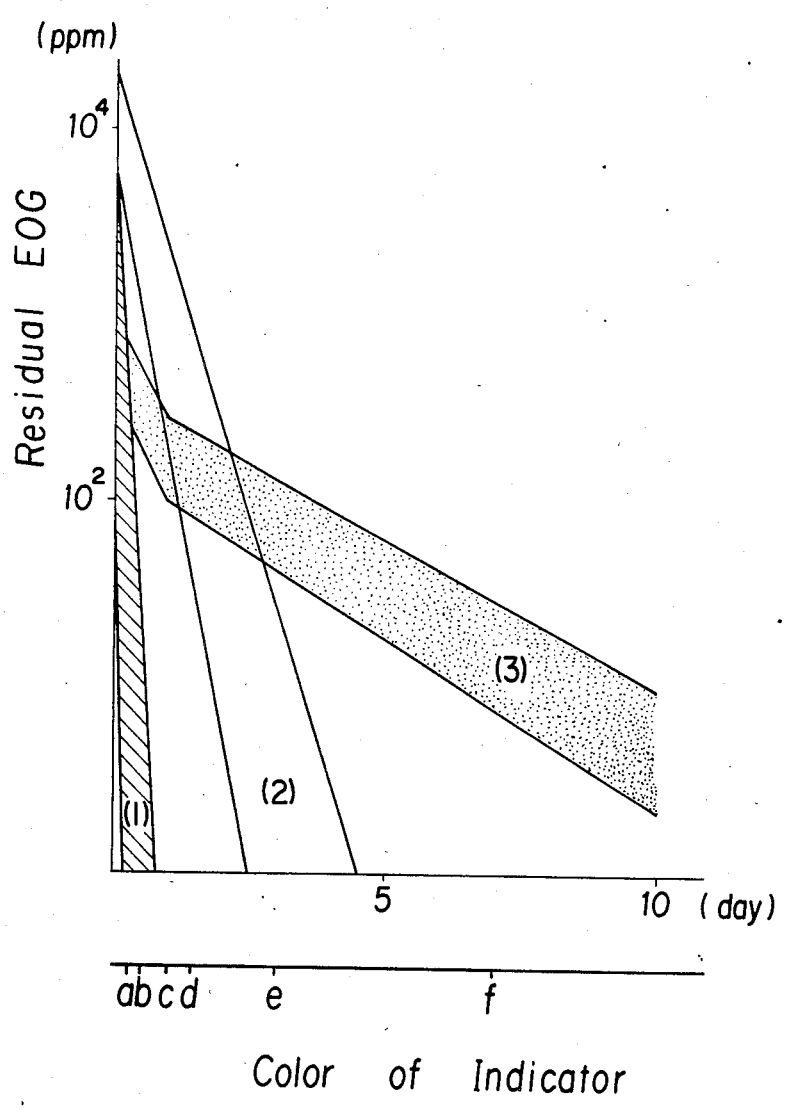
FIG. 6 shows diagrams illustrating respectively the relationship between the concentration of residual EOG and the course of release of EOG from sterilized materials at 25° C. with the colour change of the indicator of the invention.

| Time in days | 0 | 0.25 | 0.5 | 1 | 1.5 | 3 | 7 |
|---|---|---|---|---|---|---|---|
| Colour | — | light blue | blue | dark blue | grey | brown | light brown |
| Letter of FIG. 6 | | a | b | c | d | e | f |

EXAMPLE 2

The indicator prepared as in Example 1 was packed into a sterilizing package made of a plastic film and a synthetic film together with each of the following materials for medical instruments such as polyethylene, polystyrene, polypropylene, polycarbonate, ABS, polyacetal, 6-nylon, 6,6-nylon, plasticized polyvinylchloride, latex-rubber, butadiene-rubber and silicone-rubber, and these packages were treated under the same conditions as in Example 1. After sterilization, the packages were removed from the sterilizer and was left in a room at 25° C., and the concentration of residual EOG in the material was determined by gas chromatography as the time passed by, while the color change of the indicators were observed.

The colour change of the indicator was the same as in Example 1 as shown in FIG. 6, wherein the letter from a to f corresponds to each colour from light blue to light brown respectively.

As seen from FIG. 6, the course of release of EOG from the material was classified in three groups, namely, the first group of latex-rubber, butadiene-rubber and silicone-rubber shown as (1) in FIG. 6 from which EOG was easily released, the second group of polyethylene and plasticized polyvinyl chloride shown as (2) in FIG. 6 from which EOG was moderately easily released, and the third group of 6,6-nylon, 6-nylon, polycarbonate, polystyrene, polypropylene, ABS and polyacetal from which EOG was difficultly released.

In the material from which EOG was most difficultly released in each of the three groups, namely butadiene rubber in the first group, polyethylene in the second group and ABS in the third group, the colours of the indicator of the invention corresponding to the upper limit of the residual EOG in the regulated values of FDA were shown in Table 2.

TABLE 2

| Group | less than 250 ppm | less than 25 ppm |
|---|---|---|
| First | light blue | blue |
| Second | grey | brown |
| Third | dark blue | light brown |

EXAMPLE 3

After the same indicator as in Example 1 and each of the same medical materials as in Example 2 were subjected to the same conditions of sterilization, the indicator and the medical materials were transferred into an airator kept at 50° C. with an air ventilation rate of 500 liters/min. and the colour change of the indicator was observed.

According to the results, the course of release of EOG could be classified into three groups, however, the time required for the concentration of residual EOG to be the predetermined value was about one fifth of the time in Example 2 with the same pattern of colour-change of the indicator appearing within the equally shortened time.

What is claimed is:

1. An indicator for estimating concentrations of ethylene oxide remaining in medical instruments or sanitary goods during or after aeration following sterilization of said instruments or goods with ethylene oxide comprising:
    (a) a substrate formed by impregnating a paper body with a solution consisting of about 0.5–5% by weight of 4-(4- nitrobenzyl)-pyridine in an organic solvent and removing said solvent; and (b) an envelope enclosing said substrate, said envelope comprising a transparent, heat-sealable single layer or composite plastic film having a low permeability to ethylene oxide and a permeability to carbon dioxide of not more than about 200 ml/100 in $^2$/mil/24 hours at 25° C. under 1 atmosphere and at 50% relative humidity, said substrate sequentially changing color step-wise following the exposure of the indicator to ethylene oxide gas, with the color change of said substrate during the aeration being controlled by said envelope having a low permeability to ethylene oxide.

2. The indicator of claim 1, in which the plastic film is made of polyvinyl alcohol or nylon.

3. The indicator of claim 1 wherein the plastic film comprises a composite film comprising an outer layer having low permeability to gaseous ethylene oxide and an inner layer having heat-sealability and high permeability to gaseous ethylene oxide.

4. The indicator of claim 3 wherein the outer layer is formed from a material selected from the group consisting of polyester, nylon, polyvinyl alcohol, polyvinylidene chloride, polyvinyl fluoride and cellophane.

5. The indicator of claim 3 wherein the inner layer comprises polyethylene or polypropylene.

6. The indicator of claim 3 wherein the composite film comprises a polyester film as an outer layer and a polypropylene film as an inner layer.

7. The indicator of claim 3 wherein the outer layer is formed from a material selected from the group consisting of polyester, nylon, polyvinyl alcohol, polyvinylidene chloride and polyvinyl fluoride.

8. The indicator of claim 1 wherein the envelope comprises a base plate made of metal foil and a plastic film having low permeability to gaseous ethylene oxide, the substrate being enclosed therebetween.

9. The indicator of claim 1 wherein the paper body is selected from the group consisting of filter paper, synthetic paper and blotting paper.

10. The indicator of claim 1 wherein the substrate is in the form of a strip, flake or tablet.

* * * * *